United States Patent
Greif

(10) Patent No.: US 9,399,037 B2
(45) Date of Patent: Jul. 26, 2016

(54) TRIAZINONE COMPOUNDS FOR TREATING DISEASES RESULTING FROM INFESTATION WITH PARASITIC PROTOZOANS

(75) Inventor: Gisela Greif, Remagen (DE)

(73) Assignee: Bayer Intellectual Property GmbH (DE)

( * ) Notice: Subject to any disclaimer, the term of this patent is extended or adjusted under 35 U.S.C. 154(b) by 389 days.

(21) Appl. No.: 11/871,302

(22) Filed: Oct. 12, 2007

(65) Prior Publication Data

US 2009/0181040 A1   Jul. 16, 2009

Related U.S. Application Data

(62) Division of application No. 10/148,334, filed as application No. PCT/EP00/11837 on Nov. 21, 2000, now abandoned.

(30) Foreign Application Priority Data

Dec. 3, 1999  (DE) .................................. 199 58 388

(51) Int. Cl.
    *A01N 43/00*   (2006.01)
    *A61K 31/33*   (2006.01)
    *A61K 31/53*   (2006.01)
    *A01N 43/66*   (2006.01)
    *A01N 43/707*  (2006.01)

(52) U.S. Cl.
    CPC ................ *A61K 31/53* (2013.01); *A01N 43/66* (2013.01); *A01N 43/707* (2013.01)

(58) Field of Classification Search
    None
    See application file for complete search history.

(56) References Cited

U.S. PATENT DOCUMENTS

| | | | |
|---|---|---|---|
| 4,631,278 | A | 12/1986 | Boeckx et al. |
| 4,778,887 | A | 10/1988 | Boeckx et al. |
| 4,933,341 | A | 6/1990 | Lindner et al. |
| 4,935,423 | A | 6/1990 | Lindner et al. |
| 5,114,938 | A | 5/1992 | Lindner et al. |
| 5,141,938 | A | 8/1992 | Lindner et al. |
| 5,188,832 | A | 2/1993 | Mehlhom et al. |
| 5,196,562 | A | 3/1993 | Lindner et al. |
| 5,256,632 | A | 10/1993 | Wolf et al. |
| 5,464,837 | A | 11/1995 | Melhorn et al. |
| 5,830,893 | A | 11/1998 | Russell |
| 5,883,095 | A | 3/1999 | Granstrom et al. |
| 6,034,116 | A * | 3/2000 | Assmann et al. .............. 514/394 |
| 6,194,408 | B1 * | 2/2001 | Kennedy ......................... 514/241 |
| 6,248,329 | B1 | 6/2001 | Chandrashekar et al. |
| 6,465,460 | B1 | 10/2002 | Hundley et al. |
| 6,656,479 | B2 | 12/2003 | Brake et al. |

FOREIGN PATENT DOCUMENTS

| | | | | |
|---|---|---|---|---|
| WO | WO 9843644 A1 * | 10/1998 | ............ | A61K 31/53 |
| WO | 0019964 | 4/2000 | | |
| WO | 0037063 | 6/2000 | | |
| WO | 0037064 | 6/2000 | | |

OTHER PUBLICATIONS

Stafford et al. (New Zealand Veterinary Journal, 1994, 42, 117-119).*
Costa et al. (International Journal for Parasitology, 2008, 38, 157-159).*
Buxton (Veterinary Research, BioMed Central, 1998, 29, 289-310).*
Johnston (BMJ, Sep. 1998, 317, 665-667).*
Haberkorn, "Chemotherapy of Human and Animal Coccidioses: State and Perspectives." Database Biosis Online!, 1996, 193-199, vol. 82, No. 3, Biosciences Information Service, Philadelphia, PA, US.
Toyoharu, "Effect of Sulfamethopyrazine and Combined Use of Vaccine on Acute Toxoplasmosis in Mice," Database Chemabs 'Online!, 1971, 132-8, vol. 20, No. 2, Chemical Abstracts Service, Columbus, Ohio, US.
Lindsay, et al., "Examination of the Activities of 43 Chemotherapeutic Agents Against Neospora Caninum Tachyzoites in Cultured Cells," American Journal of Veterinary Research, Jul. 1994, 976-981, vol. 55, No. 7.
Gottstein, "Zystenbildende Kokzidien: Toxoplasma, Neospora, Sarcocystis," Schweizerisch Medizinische Wochenschrift, May 6, 1995, 890-898, vol. 125, No. 18, Basel, CH.
Pipano, "Live Vaccines Against Hemoparasitic Diseases in Livestock," Veterinary Parasitology, Mar. 1, 1995, 213-231, vol. 57, No. 1/03, Elsevier Science, Amsterdam.
PCT International Search Report dated Jun. 22, 2001, 9 pgs.
Herbert, Dictionary of Immunology 4th Ed., Academic Press 1995, 58-59.
Ellis, R.W., Chapter 29 of "Vaccines" Plotkin, S.A. et al. (EDS) Published by W.B. Saunders Company (Philadelphia) in 1988, 568-575.
Janeway-Travers, 1997, Immunology: The Immune System in Health and Disease, 3rd Edition.
Haerdi, et al., Humoral Immune Response of Newborn Calves Congenitally Infected With Neospora Caninum and Experimentally Treated With Toltrazuril, Parasitol Res, 2006, 534-540, vol. 99.
Gottstein, et al., Toltrazuril Treatment to Control Diaplacental Neospora Caninum Transmission in Experimentally Infected Pregnant Mice, Parasitology, 2005, 41-48, vol. 130.
Lindsay, et al., Effects of Sulfadiazine and Amprolium on Neospora Caninum (Protozoa: Apicomplexa) Infections in Mice, J. Parasitol., 1990, 177-179, vol. 76, No. 2.
Lindsay, et al., Infections in Mice With Tachyzoites and Bradyzoites of Neospora Caninum (Protozoa: Apicomplexa), J. Parasitol., 1990, 410-413, vol. 76, No. 3.

* cited by examiner

*Primary Examiner* — Dennis Heyer
*Assistant Examiner* — Daniel M Podgorski
(74) *Attorney, Agent, or Firm* — Senniger Powers LLP

(57) ABSTRACT

The present invention relates to the use of triazinones such as triazinediones and triazinetriones for triazinetriones for the preparation of compositions for treating animals, in particular treating animals prophylactically, against parasitic protozoans, and to these compositions.

16 Claims, No Drawings

TRIAZINONE COMPOUNDS FOR TREATING DISEASES RESULTING FROM INFESTATION WITH PARASITIC PROTOZOANS

The present invention relates to triazinone compounds for treating, in particular prophylactically, animals which are infected with parasites which lead to fetus loss or cause nerve diseases. In particular, the present invention relates to those triazinone compounds which are suitable for treating parasitic protozoans such as coccidia which lead to fetus loss or cause nerve diseases. Very especially, the present invention relates to those triazinone compounds which are suitable for treating Neospora infections.

Triazinone compounds such as triazinediones, for example diclazurils, and triazinetriones, for example toltrazurils, were used for treating a wide range of mammals, insects and fish against diseases caused by a wide range of protozoans; see U.S. Pat. Nos. 4,631,218; 4,933,341; 4,935,423; 5,114,938; 5,141,938; 5,188,832, 5,196,562, 5,256,631 and 5,464,837 or else EP A 170 316. The protozoans which are sensitive to these compounds include parasites which infect the viscera of birds, mammals and insects manifested in the form of diarrhea, lack of vigor, nausea and vomiting. In general, the mode of action of the triazinones consists in attacking the intermediate stages of the parasite present in the intestinal wall cells and visceral wall cells, whereby the endoplasmic reticulum, the zone surrounding the nucleus and the mitochondria of the parasites enlarge. This probably interferes with the ability of the nucleus to divide, whereby the schizonts and microgamonts remain small and only form in each case a few merozoites and microgametes. The final result is that these later parasitic stages lose the ability of penetrating new mammalian cells, whereby multiplication of the parasite in the host is prevented effectively.

Certain protozoans which have been though since the 70s to cause nerve diseases and/or lead to fetus loss in animals are of particular importance. The successful isolation and in-vitro culture of some of these protozoans proved to be difficult. For example, it was only in the late 80s that cerebral fluid or spinal fluid were isolated successfully. As soon as there was no doubt that nerve diseases can be caused by parasites which infect the brain, and diseases leading to fetus loss can be caused by the fetus-infecting parasites, there was a need of effective antiprotozoel drugs which are capable of crossing the blood-brain barrier and the placental barrier without causing damaging side effects. Only a very small number of drugs are capable of crossing the blood-brain barrier or the placental barrier of animals. Many of the prior-art drugs which are capable of crossing the blood-brain barrier and/or the placental barrier in order to effectively treat parasitic brain infections have damaging side effects and can therefore not be used without posing a high risk. No effective drugs which constitute an effective treatment of such nerve diseases and diseases which lead to fetus loss have therefore been approved to date. What follows is a brief description of the diseases caused by parasites.

*Neospora caninum* is a new parasite from the group of the protozoans which was first described in a Norwegian dog in 1984 by BJERKAS et al. Natural infections, apart from in dogs and cattle, have also been found in sheep, goats and horses (Dubey and Rommel 1992, Dubey and Lindsay 1993). Apart from dogs and cattle, foxes, cats, sheep and mice were also successfully infected experimentally. The definitive host of *Neospora caninum* is probably the dog (McAllister et al. 1998), but no detailed studies into the complete life history are available as yet.

Many different cells may act as host cells for *Neospora caninum*, for example macrophages, neutrophils, fibroblasts, endothelial cells of blood vessels, myocytes, epithelial cells of the renal tubules, hepatocytes and nerve cells. However, the reproduction via tachyzoites preferably takes place in organelles such as muscle and nerve cells. It is therefore in these tissues that the pathological symptoms following natural infection predominate. Dogs aged 5 to 6 weeks and over which are infected naturally thus show disease symptoms with signs of oversensitivity due to radiculitis and increasing lameness of the hind legs. Further histopathological abnormalities are found in the nervous system, predominantly in the brain and spinal cord. Here, extensive non-suppurative inflammations, proliferations of the glia and perivascular infiltrations with mononuclear cells (macrophages, lymphocytes, some plasma cells), in some cases also eosinophils and neutrophils, predominate. Necrotic-degenerative changes in the musculature can even be seen with the naked eye. What is noticed is, besides more or less pronounced atrophy, long pale longitudinal stripes. This applies in particular to the hind legs. Histologically, the changes constitute a pronounced myocytis with minor necroses and non-suppurative vesiculitis. These changes are also observed in less pronounced form in the musculature of the front legs, the diaphragm, and the lingual musculature. Dogs aged 5 to 12 weeks which have these symptoms must be euthanized (Dubey et al. 1988). *Neospora* infections are transmitted to the next generation by repeated transplacental transmission. The disease does by no means necessarily affect all of the animals in one litter. When 6 bitches were experimentally infected on day 21 of the pregnancy, 1 bitch gave birth to 3 live puppies while the other 5 *N. caninum*-positive fetuses aborted. The parasite was not detectable in the 3 puppies which had been born alive (Cole et al. 1995).

The first ever description in cattle was by Thilsted and Dubey (1989) in the brain tissue of a miscarried fetus from New Mexico. Further isolations from cattle were performed in the United States (Conrad et al. 1993, Barr et al. 1993, Marsh et al. 1995), Japan (Yamane et al. 1996) and Sweden (Stenlund et al. 1996). In California and Australia, *Neospora caninum* infections are considered the main cause for fetus losses in herds of cattle (Barr et al. 1990).

It is likely that by far the most *Neospora*-infected calves are miscarried when aged 3 to 9 months. In these fetuses, it is mainly tachyzoites which are found in substantial numbers. As yet, cysts were only evidenced in calves which had been born. Infected calves die at the latest 3 to 17 days post-partum. The disease symptoms are similar to those in dogs. Ataxias are observed, the articular reflexes are greatly reduced, and lameness of the hind legs, in some cases of all four legs, is observed. The histological findings are similar to those in dogs: non-suppurative meningitis and myelitis predominate. As is the case in dogs and other animals, mononuclear cell infiltrates necroses were found in the brain, in particular in perivascular zones. Parasites, in particular tachyzoites or pseudocysts with tachyzoites, are found in particular—but mostly in small numbers, as foci in nerve tissue, in rare cases also in muscle cells. What is noticeable, and in clear contrast to *Toxoplasma*, is the fact that *Neospora* can be transmitted repeatedly from a dam to the progeny. This has been evidenced in dogs and cattle (Bjerkas et al. 1984, Dubey and Rommel 1992, Dubey et al. 1988).

A comparison between *N. caninum* isolates from dogs and cattle have so far not revealed any differences, neither at the level of the morphological ultrastructure, protein analysis nor following molecular-biological sequence alignment of the rRNA or ITS1 sequence (Holmdahl and Mattsson 1996).

Distribution and Economic Importance

Since *N. caninum* was discovered in 1984, it has been identified all over the world (Review Dubey/Lindsay). In the case of California, the proportion of fetus losses in cows caused by *N. caninum* is estimated as being particularly high. Of 468 miscarried fetuses, 45.5% were due to *Neospora caninum* infection (Dubey and Lindsay 1993). In Switzerland, *Neospora*-specific DNA was detected in the brain of 29% of miscarried fetuses; accordingly, the annual losses are estimated at 10.2 million Swiss francs (Gottstein/Bern) and 100 million dollars in Australia (Johnson/Sydney). In California, the disease incidence peaks during winter from December to February. Analogous findings were obtained for New Zealand (Thornton et al. 1991). Here, most of the miscarriages caused by *N. caninum* were reported from May to July. An effective method of treating *N. caninum* infections, in particular prophylactically, has hitherto not been disclosed.

Equine protozoal myeloencephalitis (EPM) is a neurological disease found mainly in young horses under stress (for example thoroughbred racehorses and pure-bred performance horses) and is therefore a disease with substantial financial impact on the equestrian economy. EPM, which was identified first as a disease in the 70s, was cultured as late as 1991 from an EPM horse and named *Sarcocystis neurona*. In 1997, a *Neospora* spp., which is now termed *Neospora hugesi*, was isolated from the brain of an EPM horse. Accordingly, it is now proposed that EPM might be caused only by this newly identified organism, only by *Sarcocystis neurona*, or by a combination of these organisms. Most frequently, EPM results in asymmetric ataxia, weakness and spasticity. The disease can mimic any neurological condition. The disease may occur in peracute or chronic form. The chronic form is often insidious in onset, difficult to diagnose until late in disease, and may culminate in death. In the mildest cases, the only clinical sign may be an ill defined hip limb lameness or a minor respiratory noise. In the most severe cases, the horses are unable to swallow or stand. It is now known that, in the most severe cases, the parasite, for example *S. neurona*, infects the brain, where it causes considerable damage. The clinical signs are caused by direct neuronal damage (in the brain and spinal cord) by the parasite, and brain damage owing to infiltration of inflammatory cells, edema, and nerve death in the central nervous system (CNS) associated with merozoites and merontes. There is currently no effective prophylaxis for controlling EPM. The combination of the drugs trimethoprim and sulphonamide, which are approved for use in humans, was used. However, the treatment is expensive and requires many repeat doses.

A further parasite belonging to the group of the coccidia, *Toxoplasma gondii*, has been known for some time and was first isolated from the viscera and muscle tissue of a cat. The definitive host of this parasite is the cat, which may harbor the organism over a prolonged period, while the oocysts spread to other animals including cattle, sheep, pigs and humans. The infection of sheep, cattle and humans has been associated with diseases leading to fetus loss and with congenital diseases which mainly attack the central nervous system. In most recent times, it has also been associated with the fetus loss and malformations on kittens from an infected dam which was seronegative during the pregnancy prior to infection. Non-cat hosts such as cattle, sheep, pigs and humans produce no oocysts, but tachyzoites and bradyzoites develop and the muscles and brain may be invaded by these, the tachyzoites and bradyzoites causing the clinical signs of the disease, which are neurological symptoms and fetus loss with fetal malformations. It has been reported that 60% of all cats are serologically positive for *T. gondii*. Again, no treatment, in particular no prophylactic treatment, of toxoplasmosis exists.

The use of triazinone compounds such as diclazuril, toltrazuril or toltrazuril sulphone (recently known under the new name "ponazuril") for the treatment, in particular the prophylactic treatment, without unacceptable side effects of animals exposed to risk of infection with coccidia, in particular from the family Sarcocystidae, is not disclosed in the prior-art literature, including the literature mentioned at the outset, or is not taught therein. It was therefore an object to provide an effective treatment, in particular prophylactic treatment, for animals which are exposed to a risk of infection with the abovementioned parasites.

Surprisingly, it has now been found that a far-reaching protection from infections with parasitic protozoans is achieved by using triazinones for the treatment, in particular the prophylactic treatment.

Accordingly, the present invention relates to a method of treating, in particular prophylactically, an animal which is exposed to the risk of infection with parasitic disease which manifest themselves as neurological disease or a disease leading to fetus loss, characterized in that a pharmaceutically active amount of a triazinone compound is applied to the animal. Such animals are, by way of example but not by limitation, horses, cattle, cats, dogs, pigs, sheep, birds, insects and humans.

The parasites which cause the infection or disease are coccidia of the family Sarcocystidae, which may manifest themselves as neurological diseases or diseases which lead to fetus loss. For illustration, examples which are not to be classed as limiting may be selected from the group consisting of *Sarcocystis* spp., *Neospora* spp. and *Toxoplasma* spp. Typically, the Sarcocystidae are selected from the group consisting of *S. neurona*, *N. hugesi*, *N. caninum* and *T. gondii*, in particular from the group *Neospora* spp. The protozoal infections or protozoal diseases include EPM, neosporosis and toxoplasmosis, but they are not limited thereto.

Upon carrying out the invention, the treatment, in particular the prophylactic treatment, of the animals against the parasitic infections or diseases caused by the protozoans described herein lead to the prevention of the symptoms and the diseases associated therewith. In general, the symptoms of these diseases include lameness, ataxia, paralysis, fetus loss, weak newborns, and other related disorders. Typically, the treatment takes approximately 1 to 30 days, preferably approximately 1 to 20 days, especially preferably 1 to 10 days and very especially preferably 1 to 6 days. Naturally, the treatment scheme for the treatment, in particular the prophylactic treatment, may be once per day, twice per day or several times per day, once every other day or indeed once per week, depending on the circumstances and the species of the pathogenic parasite.

Preferred dosages are 1-500 mg of active compound per kg of body weight of the animal to be treated, especially preferred are doses from 10 to 200 mg/kg, and very especially preferred are doses from 20-150 mg/kg.

Without wanting to be bound to one specific theory, it is assumed that the unexpected success of the treatment, in particular the prophylactic treatment, described herein is due to the ability of the triazinone compounds to cross the blood-brain barrier or the placental barrier. It is assumed that the compounds of the present invention readily cross the blood-brain barrier and are also capable of penetrating into the placenta and kill the protozoans in situ in the brain and in the spinal fluid in the spinal cord.

Hitherto, no inexpensive readily administered drugs were available for the effective protection against these diseases without unacceptable side effects such as toxicity or mutagenicity in animals. The triazinone compounds will now be described in the text which follows, in particular with regard to toltrazuril compounds, but not by way of limitation. The present disclosure and the invention claimed furthermore comprise other triazinone compounds which are useful in the sense of the toltrazuril compounds.

The triazinetriones, toltrazurils, which can be used in accordance with the invention have the formula (I)

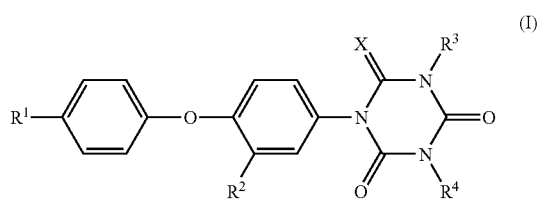

(I)

in which
R$^1$ is halogenoalkylthio, halogenoalkylsulfynyl or halogenoalkylsulfonyl,
R$^2$ is hydrogen, alkyl, alkoxy, alkoxyalkyl, alkylmercapto, halogen, halogeno-alkyl or an optionally substituted sulfamoyl radical, such as dialkylsulfamoyl radical, and
R$^3$ and R$^4$ can be identical or different and represent halogen, alkyl, alkenyl or alkynyl, and X represents O or S, and their physiologically acceptable salts.

Furthermore, it has been found that in particular the following triazinetriones, toltrazurils of the formula (I), in which
R$^1$ represents halogeno($C_1$-$C_4$)alkylthio, halogeno($C_1$-$C_4$)alkylsulfynyl or halogeno($C_1$-$C_4$)alkylsulfonyl,
R$^2$ represents hydrogen, ($C_1$-$C_4$)alkyl, ($C_1$-$C_4$)alkoxy, halogen, ($C_1$-$C_4$)alkoxy-($C_1$-$C_4$)alkyl, ($C_1$-$C_4$)alkylmercapto, ($C_1$-$C_4$)dialkylaminosulfonyl or halogeno-($C_1$-$C_4$)alkyl and
R$^3$ and R$^4$ can be identical or different and represent hydrogen ($C_1$-$C_4$)alkyl or ($C_1$-$C_4$)alkenyl and X represents O or S, can be used in accordance with the invention.

The triazinediones, diclazurils, which can also be used in accordance with the invention have the formula (Ia)

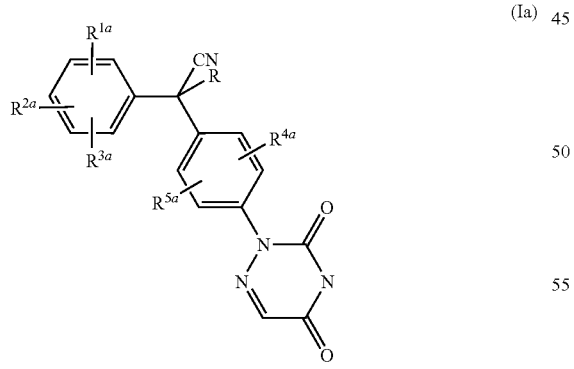

(Ia)

in which
R$^{1a}$, R$^{2a}$ and R$^{3a}$ in each case independently of one another represent hydrogen, halogen, trifluoromethyl, $C_1$-$C_6$-alkyl, $C_1$-$C_6$-alkyloxy, $C_1$-$C_6$-alkylthio or $C_1$-$C_6$-alkylsulfonyl,
R$^{4a}$ and R$^{5a}$ in each case independently of one another represent hydrogen, halogen, trifluoromethyl or $C_1$-$C_6$-alkyl, and R represent hydrogen, $C_1$-$C_6$-alkyl, cyclo-$C_3$-$C_6$-alkyl or phenyl which optionally with up to 3 substituents selected independently of one another from the group consisting of halogen, trifluoromethyl, $C_1$-$C_6$-alkyl, $C_1$-$C_6$-alkyloxy, $C_1$-$C_6$-alkylthio or $C_1$-$C_6$-alkylsulfonyl.

Compounds of the formula (Ia) which are preferably used are those in which
R$^{1a}$ and R$^{2a}$ in each case independently of one another represent hydrogen, halogen, trifluoromethyl or $C_1$-$C_6$-alkyl,
R$^{3a}$ represents hydrogen,
R represents hydrogen, $C_1$-$C_6$-alkyl, phenyl or halogenophenyl, and
R$^{4a}$ and R$^{5a}$ in each case independently of one another represent hydrogen, halogen, trifluoromethyl or $C_1$-$C_6$-alkyl.

Compounds of the formula (Ia) which are particularly preferably used are those in which
R$^{1a}$ represents 4-halogeno,
R$^{2a}$ and R$^{3a}$ represent hydrogen,
R represents hydrogen or methyl, and
R$^{4a}$ and R$^{5a}$ in each case independently of one another represent hydrogen, halogen or trifluoromethyl, where R$^{4a}$ and R$^{5a}$ are in the 2- and 6-position of the phenyl radical to which they are attached.

Compounds which are especially preferably used are, specifically,

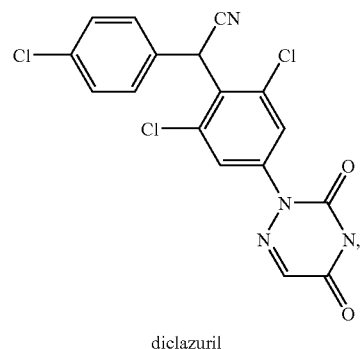

diclazuril

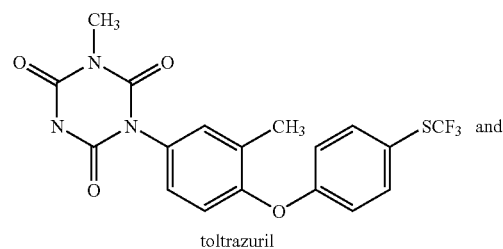

toltrazuril

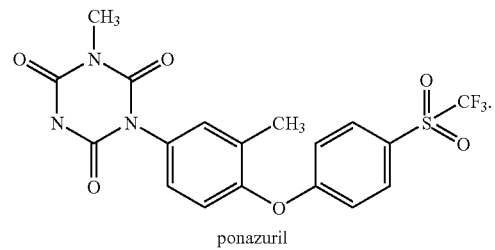

ponazuril

The compounds toltrazuril and ponazuril are very especially preferably used.

Furthermore, it has been found that
(a) the compounds of the formula I are obtained when compounds of the formula II

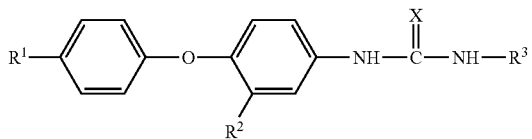 (II)

in which
R$^1$, R$^2$, R$^3$ and X have the abovementioned meanings are reacted with a substituted carboxylic acid isocyanate of the formula III

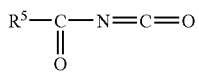 (III)

in which
R$^5$ represents a halogen atom, an alkoxy group or an aryloxy group, and the resulting substituted 1,3,5-triazine derivatives of the formula IV

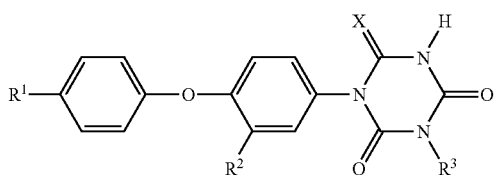 (IV)

in which
R$^1$, R$^2$, R$^3$ and X have the abovementioned meanings, are, if appropriate, isolated and, if appropriate, reacted with a compound of the formula V

A-Z (V)

in which
A represents alkyl, alkenyl or alkynyl and
z represents halogen;
or that
(b) compounds of the formula I are obtained when compounds of the formula II in which R$^1$, R$^2$, R$^3$ and X have the abovementioned meanings are reacted with bis(chlorocarboxylic acid)amines of the formula VI

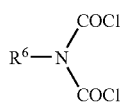 (VI)

in which
R$^6$ represents alkyl, if appropriate in the presence of acid acceptors,
or in that
(c) to obtain compounds of the formula I in which the substituents R$^2$, R$^3$ and R$^4$ and X have the abovementioned meanings and R$^1$ is halogenoalklylsulfynyl or halogenoalkylsulfonyl, compounds of the formula

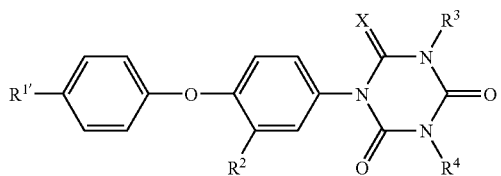 (VII)

in which
R$^2$, R$^3$ and R$^4$ have the abovementioned meanings and
R$^{1'}$ is halogenoalkylthio,
are reacted with the suitable amount of a suitable oxidant.

If, in process variant (a), N-[3-chloro-4-(4'-trifluoromethylthiophenoxy)-phenyl]-N'-methylurea and chlorocarbonyl isocyanate are used, the course of the reaction may be expressed by the following equation:

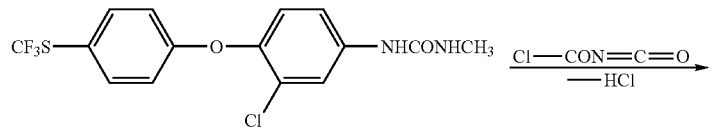

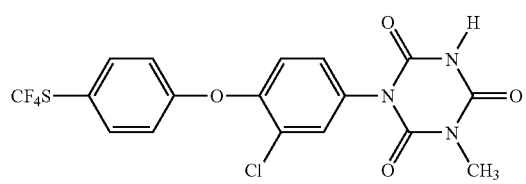

If, in process variant (b), N-[3-ethoxy-4-(4'-trifluoromethylthiophenoxy)-phenyl]-thiourea and N-methyl-bis-(chlorocarboxylic acid)amine are used as starting materials, the course of the reaction may be represented by the following equation:

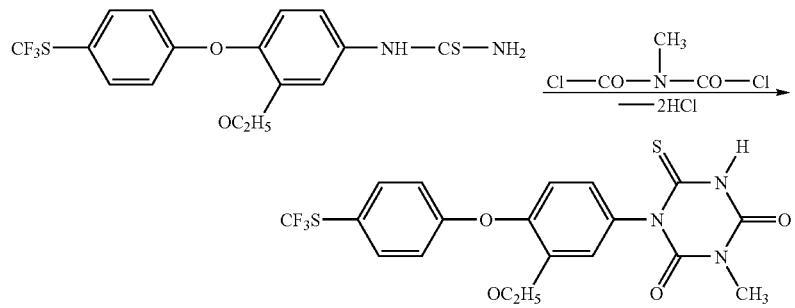

The compounds of the formula I in which $R^1$ denotes halogenoalkylthio and X denotes O and which are obtained in accordance with process variant (a) or (b) can be oxidized in accordance with process variant (c) to give the corresponding halogenoalkylsulfynyl or halogenoalkylsulfonyl derivatives. If hydrogen peroxide is used as the oxidant, the course of the process may be shown by the following equation:

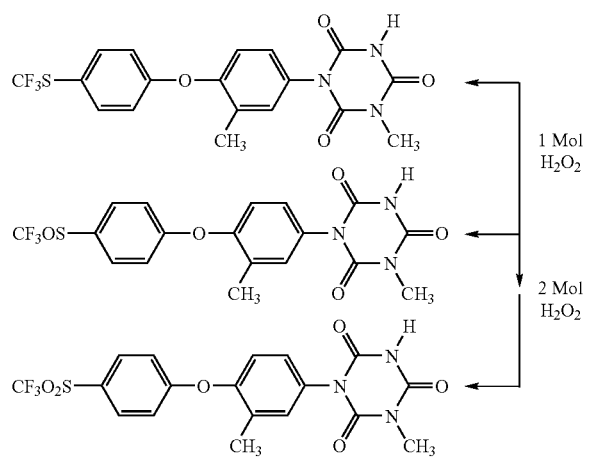

In formulae I, II, IV, V, VI and VII, the alkyl defined in $R^2$, $R^3$, $R^4$, $R^6$ or A is straight-chain or branched alkyl with preferably 1 to 6, in particular 1 to 4, carbon atoms. Examples which may be mentioned are optionally substituted methyl, ethyl, n- and i-propyl and n-, i- and t-butyl.

In formulae I, II, IV, V and VII, alkenyl defined for $R^3$, $R^4$ or A denotes straight-chain or branched alkenyl with preferably 2 to 6, in particular 2 to 4, carbon atoms. Examples which may be mentioned are optionally substituted ethenyl, propen-1-yl, propen-2-yl and buten-3-yl.

In formulae I, II, IV, V and VII, alkynyl defined for $R^3$, $R^4$ or A denotes straight-chain or branched alkynyl with preferably 2 to 6, in particular 2 to 4, carbon atoms. Examples which may be mentioned are optionally substituted ethynyl, propyn-1-yl, propyn-2-yl and butyn-3-yl.

In formulae I, II, III, IV and VII, alkoxy defined for $R^2$ or $R^5$ denotes straight-chain or branched alkoxy with preferably 1 to 6, in particular 1 to 4, carbon atoms. Examples which may be mentioned are optionally substituted methoxy, ethoxy, n- and i-propoxy and n- and i-butoxy.

In formulae I, II, III, IV, V and VII, halogen defined for $R^2$, $R^5$ or Z denotes preferably fluorine, chlorine, bromine and iodine, in particular chlorine and bromine.

In formulae I, II, IV and VII, halogenoalkylthio defined for $R^1$ is with preferably 1 to 4, in particular 1 or 2, carbon atoms, and preferably 1 to 5, in particular 1 to 3, identical or different halogen atoms, the halogen atoms preferably being fluorine, chlorine and bromine, in particular fluorine and chlorine. Examples which may be mentioned are trifluoromethylthio, chlorodifluoromethylthio, bromomethylthio, 2,2,2-trifluoroethylthio and pentafluoroethylthio.

In formulae I, II and IV, halogenoalkylsulfynyl defined for $R^1$ denotes halogeno-alkynylsulfynyl with preferably 1 to 4, in particular 1 or 2, carbon atoms and preferably 1 to 5, in particular 1 to 3, identical or different halogen atoms, the halogen atoms preferably being fluorine, chlorine and bromine, in particular fluorine and chlorine. Examples which may be mentioned are trifluoromethylsulfynyl, chlorodifluoromethylsulfynyl, bromomethylsulfynyl, 2,2,2-trifluoroethylsulfynyl and pentafluoroethylsulfynyl.

In formulae I, II and IV, halogenoalkylsulfonyl defined for $R^1$ denotes halo-genoalkylsulfonyl with preferably 1 to 4, in particular 1 or 2, carbon atoms and preferably 1 to 5, in particular 1 to 3, identical or different halogen atoms, the halogen atoms preferably being fluorine, chlorine and bromine, in particular fluorine and chlorine. Examples which may be mentioned are trifluoromethylsuphonyl, chlorodifluoromethylsulfonyl, bromomethylsulfonyl, 2,2,2-trifluoroethylsulfonyl and pentafluoroethylsulfonyl.

In formulae I, II and IV, optionally substituted sulfamoyl defined for $R^2$ denotes preferably one of the following radicals:

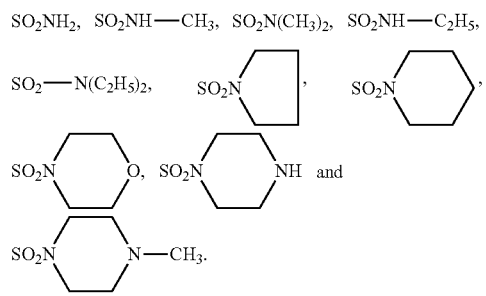

In formula III, aryloxy defined for $R^5$ denotes preferably monocyclic carbocyclic aryloxy or bicyclic carbocyclic aryloxy, in particular phenoxy.

In formula III, aryloxy in the meaning of $R^5$ denotes preferably phenoxy. Most of the substituted ureas or thioureas of the formula II which are used as starting materials were unknown to date, but can be prepared readily by processes known per se by (a) either reacting substituted 4-aminodiphenyl ethers with the corresponding substituted isocyanates or isothiocyanates in an inert solvent at temperatures between 0° C. and 100° C. or, in reverse order, (b) reacting ammonia or substituted amines and the corresponding substituted isocyanate diphenyl ethers or 4-isothiocyanate diphenyl ethers with each other under identical conditions, or by (c) subjecting substituted 4-hydroxyphenyl-ureas or -thioureas to a condensation reaction with active halogen-substituted aromatic compounds in aprotic solvents such as dimethyl sulfoxide, dimethylformamide or hexamethylphosphoric triamide in the presence of bases such as sodium hydride, potassium hydroxide, potassium carbonate and others at temperatures between 20° C. and 150° C.

When a suitable solvent is chosen, the reaction products generally crystallize upon cooling of the solution. As an alternative, however, the ureas may also be prepared from amines and isocyanates as described in the following reference: Methoden der Org. Chemie [Methods in organic chemistry] (Houben-Weyl) IVth Edition, Volume VIII, pages 157-158.

Some of the bis(chlorocarboxylic acid)-amines of the formula VI which can be used in accordance with the present invention in process (b) are already known (cf. paper in Synthesis 1970, pages 542-543), and those which were hitherto unknown can be prepared analogously from cyclic diacyl disulfides by chlorination in inert organic solvents, preferably carbon tetrachloride.

Diluents which may be used for the reaction of the ureas or thioureas of the formula II, either with the carboxylic acid isocyanates of the formula III (process variant a) or with the bis(chloro-carboxylic acid) amines of the formula VI (process variant b) and for the reaction of the 1,3,5-triazine derivatives of the formula IV with compounds of the formula A-Z are all those organic solvents which are inert toward these reactions.

Besides pyridine, they preferably include aromatic hydrocarbons such as benzene, toluene and xylene, halogenated aromatic hydrocarbons such as chlorobenzene and dichlorobenzene, and ethers such as tetrahydrofuran and dioxane.

The hydrochloric acid which may form during the reaction escapes in the form of a gas or can be bound by means of organic or inorganic acid acceptors. These acid acceptors preferably include tertiary organic bases such as trialkylamines, for example triethylamine, aromatic N-hetero (mono- or bi)cyclic amines such as mono- or bicyclic pyridineazacycloalkylamines such as diazabicyclononene, diazabicycloundecene and many others, or inorganic bases such as alkali metal carbonates, alkali metal oxides, alkali metal hydroxides, alkaline earth metal carbonates, alkaline earth metal oxides or alkaline earth metal hydroxides.

The reaction temperatures for the abovementioned reaction steps may vary within wide limits. In general, the reaction is carried out between approximately 0° C. and approximately 150° C., preferably between approximately 20° C. and approximately 100° C.

The abovementioned reaction steps may be carried out under atmospheric pressure or under elevated pressure. In general, they are carried out under atmospheric pressure.

Oxidants which are possible for the reaction in accordance with process variant (c) of the trifluoromethylthio compounds of the formula (I) in which Y represents oxygen to give the corresponding sulfynyl or sulfonyl compounds are in each case $H_2O_2$/glacial acetic acid, $H_2O_2$/acetic anhydride, $H_2O_2$/methanol, peracids such as, for example, m-chloroperbenzoic acid, and also chromic acid, potassium permanganate, sodium periodate, cerium (IV) ammonium nitrate, and nitric acid.

The preparation of the compounds of the formula (Ia) is described in EP A 170 316 and U.S. Pat. No. 4,631,278. These compounds can be obtained by the methods described therein.

A resulting compound of the formula (I) or formula (Ia) can be converted into a corresponding addition salt for example by reaction with an inorganic or organic base.

When carrying out the invention, the triazinone compound can be formulated in any desired manner to be administered to animals. Formulations which are suitable for oral administration, which is preferred in this context, may be solutions, suspensions, tablets, capsules, gels, pastes, boluses or preparations in the form of powders, granules or pellets. Further possibilities of administration are the parenteral, topical, intramuscular and intramucosal administration or other routes of administration known to the skilled worker. Topical administration in the form of a pour-on product is also preferred.

A particularly effective application is the combination of the active compounds of the formulae (I) and (Ia) with live or dead vaccines against parasitic protozoans, in particular against *Neospora* spp. Activity-enhancing effects may also be observed in such a case.

Compositions and formulations are prepared by mixing the components in suitable apparatuses such as stirred vessels and other suitable equipment.

The invention is described in greater detail by the following examples, which are given by way of illustration, but not limitation.

EXAMPLES

*Neospora Caninum* Infections

The basis of a diagnosis of *Neospora caninum*, and the delimitation to *Toxoplasma gondii* are clinical, microscopic, immune histochemical and molecular-biological parameters. Clinically, the paralysis of extremities and a repeated transplacentar transmission are observed. Tachyzoites and cysts may be seen under the microscope in musculature and nerve tissue. Cysts with a pronounced thick-walled cyst wall are found in small numbers only and exclusively in nerve tissue. Titers from 1:200 are considered specific in the indirect immunofluorescence test (IFAT) using tachyzoites produced in cell culture. Once clinical symptoms are present, titers of up to 1:20000 may be found. In terms of molecular biology, *Neospora caninum* can be identified rapidly and unambiguously by in-vitro amplification of the ITS1 region (internal transcriber spacer 1) (Holmdale and Mattsson 1996).

Description of the In-Vitro Test System

Culture of VERO Host Cells

*Neospora caninum* is an obligatory intracellular parasite. VERO cells (African green monkey kidney cells, ATCC No.: CCL 81 Vero) were used as an aid to cause the parasite to reproduce under conditions capable of standardization and definition. Vero cells were grown in the following medium: 87% RPMI 1648 (ICN, 12-602-54) 10% FCS (fetal calf serum, ICN, 29-101-49) 1% 200 mM L-glutamine (ICN, 15-801-13) 1% sodium bicarbonate (ICN, 16-883-49) 1% penicillin/streptomycin (ICN, 16-700-49). Noninfected cultures were maintained and passaged in 25 cm² (Falcon, B 769031) and 75 cm² (Falcon, B 769051) tissue culture flasks. Vero cells were grown at 37° C. in a 5% $CO_2$ atmosphere in a $CO_2$ incubator (Heraeus) until a cell monolayer was obtained.

Culture of ED Cells

ED cells (equine dermal cells, ATTC No. CCL 57) were grown in the following medium: 87% EMEM (ICN, 12-106-54) 10% FCS (fetal calf serum, ICN, 29-101-49), 1% 200 mM L-glutamine (ICN, 15-801-13), 1% NEA (non essential amino acids, Gibco, 11140-035), 1% penicillin/streptomycin (ICN, 16-70049). Noninfected cultures were maintained and passaged in 25 cm$^2$ (Falcon, B 769031) and 75 cm$^2$ (Falcon, B 769051) tissue culture flasks. ED cells were grown at 37° C. without $CO_2$ atmosphere in an incubator (Hereus) until a cell monolayer was obtained.

Cell Passage

Host cells were passaged, i.e. distributed to fresh cell culture vessels, when a culture had formed a fully confluent cell lawn. If the culture medium contained 10% FCS, this was usually the case twice per week. First, the culture medium was decanted off, the cell lawn was washed with 5 ml trypsin-EDTA (ICN, 16-891-49) and incubated for 5-10 minutes at 37° C. in a $CO_2$ incubator with a further 5 ml of trypsin-EDTA until the cells had become detached from the substrate. The trypsin-EDTA cell suspension together with 1-2 ml of pre-warmed FCS was centrifuged for 5 minutes at 1 500 rpm (Varifuge 3.0, Heraeus). The supernatant was discarded and the pellet was dissolved in 15 ml of medium (92% RPMI 1640, 5% FCS, 1% L-glutamine, 1% sodium bicarbonate, 1% penicillin/streptomycin). For each tissue culture flask, 3 new flasks were inoculated with in each case 5 ml of cell suspension, i.e. the division rate was 1:3.

Cryopreservation of Cells in Liquid Nitrogen

Cells from culture flasks were frozen either in C541 medium (50% RPMI 1640, 40% fetal calf serum (FCS), 10% dimethyl sulfoxide (DMSO, Merck 9578) or in C2 medium (86% RPMI 1640, 10% DMSO, 2% FCS, 1% L-glutamine, 1% streptomycin/penicillin). Previously, the cells were treated with trypsin as described (see above), the detached cells were centrifuged and resuspended in 3 ml of C541 freeze medium or C2 medium, and transferred into 2 ml cryotubes. Final storage was in liquid nitrogen at −196° C., where cells can be kept indefinitely. Prior to the final storage in liquid nitrogen, the cryotubes together with the cell lines were slowly cooled to −80° C. in a Styropor box with a wall thickness of 1 cm. The Styropor box allows a continuous cooling rate of 1-2° C. per minute, allowing the cells to lose their intracellular water by osmosis. This is of decisive importance for the vitality of the cells.

Defrosting Cryopreserved Cells

The defrosting process of the cryotubes from liquid nitrogen was carried out as rapidly as possible in a water bath with a temperature of 37° C. The cell suspension was pipetted in 10 ml of medium and subsequently divided uniformly into two 50 ml tissue culture flasks. The cell culture conditions were at 37° C. and 5% $CO_2$. After 24 hours, the cell culture medium was changed to remove the DMSO, which is present in the cryogenic medium.

Infection of Cell Cultures with Neospora Caninum

The following Neospora caninum isolates were used for the infection of cell cultures: NC-1 (canine isolate DUBEY (1988) and NC Swe B-1/9th passage (bovine isolate; National Veterinary Institute Uppsala, Sweden). The infection materials used were infected cell cultures from the nitrogen storage (see above) or purified tachyzoites of infected cultures (see below).

Isolation of Tachyzoites from Cell Cultures Using Sephadex

Neospora caninum was isolated from infected VERO or ED monolayers under sterile conditions. First, infected cell cultures were detached from the flask bottom using a spatula (Tec No Mara, 3010) and, using a 23-gauge cannula (Luer 23 Gx1, 0.6×25 mm) drawn into a 10 ml disposable syringe. During this procedure, host cells and tissue cysts contained therein were destroyed mechanically. The cell suspension was subsequently centrifuged for 7 minutes at 1 500 rpm (Varifuge 3.0, Heraeus), the supernatant was discarded, and the sample pellet was resuspended in precisely 2.5 ml of physiological phosphate buffer (PBS: 1 mM PO4, 12 mM NaCl, 0.87 mM KCL, pH 7.4). The next isolation step was performed using a Sephadex column (PD-10™/Sephadex G-25 M, Pharmacia Biotech, 17-0851). The column was first equilibrated with 25 ml of PBS, the sample volume was applied in 2.5 ml of PBS, and elution was then effected with 5 ml of PBS. Tachyzoites migrate rapidly through the column and are found in the first 3 ml of the eluate, while elution of high-molecular-weight cell debris and membranes from the Sephadex column lags behind. To remove undesired cell organelles and free host cell DNA, the sample was centrifuged for 7 minutes at 1 500 rpm, the supernatant was discarded, and the pellet was washed 3 times in 40 ml of PBS.

Testing Substances on Infected Neospora Caninum Cell Cultures

Substances were tested in 96-well plates (Falcon 3872) because only a small amount of starting material (approx. 1 mg) is required in this system. First, a cell culture monolayer of the host cells (Vero or ED) was established on the cell culture plates. Two 50 ml tissue culture flasks (total cell culture area 50 $cm^2$) with an established uninfected monolayer were required for this purpose. The cell lawn of this culture was detached with 5 ml of Trypsin-EDTA (Gibco, 45300-019) in the $CO_2$ incubator at 37° C. After an incubation period of 10 minutes, most of the cells had become detached. Using a 5 ml pipette, the cell suspension was transferred into a 50 ml centrifuge tube (Greiner, B769331) which had been charged with approx. 1 ml of warmed fetal calf serum. After centrifugation for 5 minutes at 1 500 rpm (Varifuge 3.0, Heraeus), the supernatant was discarded and the cell pellet was resuspended in 100 ml of RPMI medium (95% RPMI 1640, 2% FCS, 1% L-glutamine, 1% sodium bicarbonate, 1% penicillin/streptomycin). 150 μl of this cell suspension were pipetted into each well of a 96-well plate. 100 ml of medium suffice for coating 6 microwell plates. Coated cell culture plates were cultured for 24 hours in the incubator at 37° C. in 5% $CO_2$. They were then infected with purified *Neospora caninum* tachyzoites at a concentration of 48 000 tachyzoites per well and further incubation for 24 hours at 37° C. and 5% $CO_2$. The test substances were weighed into in 1.5 ml Eppendorf tubes, the weight of the substances amounting to 0.5-1.5 mg. Then, 1 ml of DMSO per mg of substance was then pipetted in, which corresponded to a dilution of $1\times10^{-3}$ g/ml. The treatment medium, in which the remaining dilution series were carried out, consisted of 87% RPMI 1640, 10% FCS, 1% L-glutamine, 1% sodium bicarbonate, 1% penicillin/streptomycin. In the first screening, the concentrations 10 ppm, 25 ppm and 50 ppm were employed. 24 hours after infection with *Neospora caninum*, the dilute preparations were transferred to the cell culture plates in a volume of 150 μl/well. In the first row, untreated medium was used, and this row contained both the infected control and the uninfected control. The cell plates were then incubated for 5 days at 37° C. and 5% $CO_2$. During this time, the tachyzoites multiply within the host cells, thus causing the destruction of the monolayer. If a substance is fully active, the tachyzoites are destroyed and the monolayer is retained. An intact monolayer can be detected in a protein binding test (live staining). One of the methods which may be used is staining with 0.25% Crystal Violet (Sigma C 3886). Before staining, the test plates were washed with 100 μl of PBS and fixed with 100 μl of methanol. Microscopical analysis was carried out 4 days after the beginning of the treatment and 5 days post-infection at the magnification of 25×10 under an inverted microscope, using the following key:

| Assessment | Visual appearance |
|---|---|
| 0 = no effect | Monolayer completely destroyed |
| 1 = some effect | Monolayer partly destroyed, parasite nests discernible |
| 2 = full action | Monolayer undestroyed, no tachyzoites discernible |
| T = cytotoxic | Cells dead, rounded up |

TABLE 1

Efficacy of toltrazuril against Neospora caninum in VERO cells

| Substance | 50 ppm | 25 ppm | 10 ppm |
|---|---|---|---|
| Infected control | 0 | 0 | 0 |
| Toltrazuril Pure active compound | 2 | 2 | 1 |
| Toltrazuril 2.5% solution* | 2 | 2 | 1 |

*100 ml of solution contained:
2.50 g toltrazuril
30.00 g triethanolamine
80.70 g polyethylene glycol,
the components are simply mixed.

| Assessment | Visual appearance |
|---|---|
| 0 = no effect | Monolayer completely destroyed |
| 1 = some effect | Monolayer partly destroyed, parasite nests discernible |
| 2 = full action | Monolayer undestroyed, no tachyzoites discernible |
| T = cytotoxic | Cells dead, rounded up |

II. In Vivo Efficacy

Only very little information is available as yet for the in-vivo efficacy of substances since adequate in-vivo test systems are still to be developed. In experimentally infected mice, sulfadiazine (administered via the drinking water) was only effective when the treatment was started prophylactically, i.e. prior to infection. In this case, clinical symptoms were prevented without a recovery in the parasitological sense taking place. A later start of the treatment was without success (Bjerkas et al. 1984, Dubey et al. 1988, Lindsay and Dubey 1989, Lindsay and Dubey 1990). In dogs, treatment with sulfadiazine and clindamycin only has a chance of success when it starts very early when the first clinical symptoms owing to reticulitis are observed.

Description of the Test Model in Mice

Dr. Simone Eperon & Prof. Bruno Gottstein, Department of Parasitology, Faculty of Veterinary Medicine and Medicine, University of Berne were commissioned by BAYER AG to plan and carry out the experimentation (Eperon et al. 1999, Parasite Immunology 21:225-236.)

Mice

Female Wt C57BL/6-mice, age at the time of treatment: 7½ weeks.

Neospora Caninum Tachyzoites

Neospora caninum tachyzoites were passaged through VERO cells, and isolated by column chromatography, and aliquots with concentrations of $2 \times 10^6$ parasites/100 µl were prepared in sterile PBS. Live staining with Trypan Blue revealed 97% viable tachyzoites.

Substances Employed for Prophylaxis (Table 2)

Pure toltrazuril active compound was made up as a stock solution with 50 mg/10 ml $H_2O$+100 µl Cremophor. 0.5 mg of pure active compound were present Der application in 0.1 ml of this solution. In a mouse of 20 g, this corresponds to a use concentration of 25 mg/kg. The substances were administered perorally by gavage on 6 successive days, which corresponds to a total uptake of 150 mg/mouse.

Toltrazuril 2.5% formulated solution (100 ml solution contain: 2.50 g toltrazuril, 30.00 g triethanolamine, 80.70 g polyethylene glycol; the components are simply mixed): 6.25 ml of the 2.5% solution were diluted in 250 ml of water and administered to the mice on 6 successive days via the drinking water.

Infection

Four hours after the start of the prophylactic treatment, each mouse was infected with $2 \times 10^6$ parasite stages/100 µl sterile PBS.

Euthanasia 14 days post-infection, the test mice were sacrificed using $CO_2$. They were numbered randomly to maintain a random sequence during evaluation (blind evaluation). To obtain serum, blood was taken from the myocardium. The brain was dissected carefully, and one half was stored at −80° C. for the PCR analysis. The remainder was fixed in 4% paraformaldehyde/PBS for immunohistological studies (IFAT).

Results

1. IgG in the Serum (Table 3)

Anti-N. caninum total immunoglobulin G (IgG) was determined by ELISA following the method of Eperon et al., 1999, Parasite Immunology 21:225-236. Treated groups were compared with an uninfected and an infected control group. The positive control mouse was inoculated with a crude extract of N. caninum tachyzoites and subsequently infected with $10^6$ N. caninum stages. The parasite-specific IgG values were particularly high in this mouse.

Mice which had been treated with toltrazuril (pure active compound) revealed a reduced concentration of Neospora caninum-specific IgG antibodies than in the infected and untreated control groups. This concentration was markedly lower in mice which had been treated with toltrazuril 2.5% formulated solution (approximating the uninfected control group).

2. PCR Analysis (Table 4)

DNA was isolated from the brain of infected mice and a Neospora caninum-specific polymerase chain reaction (PCR) was carried out as described by Eperon et al 1999, Parasite Immunology 21:225-236. All of the noninfected mice were negative in the N. caninum-specific PCR reaction. All of the infected control mice were PCR-positive. 4/7 mice in the group which had been treated prophylactically with toltrazuril pure active compound were PCR-negative. All of the mice in the group which had been treated with 2.5% formulated toltrazuril solution were PCR negative.

3. Immunofluorescence Test (IFAT, Table 4)

Paraformaldehyde-fixed brain samples were embedded in paraffin and dehydrated. Three successive sagittal sections were performed. One section was stained with hematoxilin-eosin, while the other two were processed for immunofluorescence labeling (Eperon et al., 1999. Parasite Immunology 21:225-236) with the following modifications: the first antibody was a rabbit polyclonal antibody against whole N. caninum tachyzoites with a dilution of 1:400 in 1% BSA in PBS. The second antibody was a goat-anti-rabbit FITC-labeled antibody in a concentration of 1:100 in 0.5% BSA in PBS.

No lesions or abnormal changes whatsoever were observed in all groups of the hematoxilin-eosin-stained sections, which is why immunolabeling with specific *N. caninum* antibodies was used to label stages of the parasite in brain tissue. The entire sections were studied for the assessment. Any stages of the parasite present were counted, and the following scores were used:

Score (−)=no tachyzoites
Score (+)=less than 10 tachyzoites
Score (++)=between 10 and 200 tachyzoites
Score (+++)=more than 200 parasites The score (+++) was only found in the positive control. The positive control was a knock-out mutant (μMT mouse), which produces no antibodies and died owing to the infection on day 31 post-infection. All uninfected mice were negative in the IFAT test. All toltrazuril-treated groups were negative in the IFAT test.

TABLE 2

Efficacy of toltrazuril against *Neospora caninum* in mice

| Day | Date | Toltrazuril pure active compound 25 mg/kg/day p.o. | Toltrazuril 2.5% formulation i.w. | Infected Control | Uninfected Control |
|---|---|---|---|---|---|
| BL/6 mice | | 7 mice | 5 mice | 5 mice | 5 mice |
| Day 0 | 21 Jun. 1999 | 25 mg/mouse | 2.5% i.w. | — | — |
| Infection 4 h later | 21 Jun. 1999 | 2 × 10$^6$ tachyzoites i.p. | 2 × 10$^6$ tachyzoites i.p. | 2 × 10$^6$ tachyzoites i.p. | No infection |
| Day 1 p.i. | 22 Jun. 1999 | 25 mg/mouse | 2.5% i.w | — | — |
| Day 2 p.i. | 23 Jun. 1999 | 25 mg/mouse | 2.5% i.w | — | — |
| Day 3 p.i. | 24 Jun. 1999 | 25 mg/mouse | 2.5% i.w | — | — |
| Day 4 p.i. | 25 Jun. 1999 | 25 mg/mouse | 2.5% i.w | — | — |
| Day 5 p.i. | 26 Jun. 1999 | 25 mg/mouse | 2.5% i.w | — | — |
| Day 14 p.i. | 5 Jul. 1999 | euthanasia | euthanasia | euthanasia | Euthanasia | p.i. = post infectionem
p.o. = peroral
i.w. = in water

TABLE 3

Anti-*Neospora caninum* IgG in the serum of individual mice, and mean IgG concentration in the serum per treatment group

| Experimental group | Mouse No. * | OD (anti Neospora IgG in the serum) | OD mean |
|---|---|---|---|
| Uninfected control | 242 | 0.034 | 0.0340 |
| Uninfected control | 228 | 0.03 | (+/−0.0044) |
| Uninfected control | 240 | 0.028 | |
| Uninfected control | 227 | 0.045 | |
| Uninfected control | 233 | 0.033 | |
| Infected control | 239 | 0.178 | 0.2352 |
| Infected control | 224 | 0.224 | (+/−0.0542) |
| Infected control | 246 | 0.168 | |
| Infected control | 234 | 0.242 | |
| Infected control | 222 | 0.364 | |
| Toltrazuril 25 mg/kg | 241 | 0.338 | 0.1689 |
| Toltrazuril 25 mg/kg | 225 | 0.271 | (+/−0.0807) |
| Toltrazuril 25 mg/kg | 244 | 0.056 | |
| Toltrazuril 25 mg/kg | 220 | 0.066 | |
| Toltrazuril 25 mg/kg | 231 | 0.18 | |
| Toltrazuril 25 mg/kg | 235 | 0.103 | |
| Toltrazuril 25 mg/kg | 245 | 0.168 | |
| Toltrazuril 2.5% i.w. | 230 | 0.085 | 0.0838 |
| Toltrazuril 2.5% i.w. | 238 | 0.109 | (+/−0.0254) |
| Toltrazuril 2.5% i.w. | 243 | 0.121 | |
| Toltrazuril 2.5% i.w. | 221 | 0.022 | |
| Toltrazuril 2.5% i.w. | 229 | 0.082 | |
| Positive control | 14 | 0.381 | 0.381 (+/−0) |

TABLE 4

*N. caninum*-specific PCR and IFAT

| Experimental group | Mouse No. * | Neospora PCR | IFAT |
|---|---|---|---|
| Uninfected control | 242 | − | − |
| Uninfected control | 228 | − | − |
| Uninfected control | 240 | − | − |
| Uninfected control | 227 | − | − |
| Uninfected control | 233 | − | − |
| Infected control | 239 | + | + |
| Infected control | 224 | + | + |
| Infected control | 246 | + | ++ |
| Infected control | 234 | + | − |
| Infected control | 222 | + | + |
| Toltrazuril 25 mg/kg | 241 | + | − |
| Toltrazuril 25 mg/kg | 225 | − | − |
| Toltrazuril 25 mg/kg | 244 | − | − |
| Toltrazuril 25 mg/kg | 220 | − | − |
| Toltrazuril 25 mg/kg | 231 | + | − |
| Toltrazuril 25 mg/kg | 235 | − | − |
| Toltrazuril 25 mg/kg | 245 | + | − |
| Toltrazuril 2.5% i.w. | 230 | − | − |
| Toltrazuril 2.5% i.w. | 238 | − | − |
| Toltrazuril 2.5% i.w. | 243 | − | − |
| Toltrazuril 2.5% i.w. | 221 | − | − |
| Toltrazuril 2.5% i.w. | 229 | − | − |
| Positive control | 14 | + | +++ |

* The numbers were allocated randomly to ensure unbiased evaluation; they are therefore not in logical order.

What is claimed is:

1. A method for the prophylactic treatment of an animal exposed to risk of infection with *Neospora caninum* comprising orally administering to the animal, prior to infection by parasitic protozoans, an effective amount of Toltrazuril or Ponazuril.

2. The method of claim 1, wherein the effective amount is from 1 to 500 mg of active compound per kg or body weight of the animal.

3. The method of claim 1, wherein the effective amount is from 10 to 200 mg of active compound per kg of body weight of the animal.

4. The method of claim 1, wherein the effective amount is from 20 to 150 mg of active compound per kg of body weight of the animal.

5. The method of claim 1, wherein the animal is selected from the group consisting of dog, cattle, sheep, goat, and horses.

6. The method of claim 1, wherein the animal is a dog.

7. The method of claim 1, wherein the animal is cattle.

8. The method of claim 1, wherein the animal is a sheep.

9. The method of claim 1, wherein the animal is a goat.

10. The method of claim 1, wherein the animal is a horse.

11. A method for the prophylactic treatment of an animal exposed to risk of infection with *Neospora caninum* comprising orally administering to the animal, prior to infection by parasitic protozoans, from about 10 to 150 mg of Toltrazuril per kg of body weight of the animal.

12. The method of claim 11, wherein the animal is a dog.

13. The method of claim 11, wherein the animal is cattle.

14. The method of claim 11 wherein the animal is a sheep.

15. The method of claim 11, wherein the animal is a goat.

16. The method of claim 11, wherein the animal is a horse.

* * * * *